United States Patent [19]

Minisci et al.

[11] 4,322,547
[45] Mar. 30, 1982

[54] PROCESS FOR PRODUCING DIFUNCTIONAL ALIPHATIC ORGANIC COMPOUNDS

[75] Inventors: Francesco Minisci, Milan; Paolo Maggioni, Cernusco Montevecchia; Attilio Citterio, Monza, all of Italy

[73] Assignee: Brichima S.p.A., Milan, Italy

[21] Appl. No.: 170,956

[22] Filed: Jul. 21, 1980

[51] Int. Cl.³ .................... C07C 67/10; C07C 67/22; C07C 99/00; C07C 120/00
[52] U.S. Cl. ........................ 560/204; 260/465.4; 560/155; 560/190; 562/553; 562/567; 562/590; 562/592
[58] Field of Search ............... 260/465.4; 560/190, 560/155, 204; 562/553, 567, 590, 592

[56] References Cited

U.S. PATENT DOCUMENTS 3,914,291 10/1975 Billet et al. ........................... 560/204

Primary Examiner—Natalie Trousof
Assistant Examiner—Vera C. Clarke
Attorney, Agent, or Firm—Stevens, Davis, Miller & Mosher

[57] ABSTRACT

Process industrially and economically useful for preparing difunctional aliphatic organic compounds of formula $$X-(CH_2)_n-Y$$

in which $n=6,7$, $X=-COOH$, $-COOR$, $Y=-CN$, $-COOH$, $-CONH_2$, $-CH_2-NH_2-COOR$ wherein R is a linear or branched alkyl containing 1-6 carbon atoms.

The process starts from a ketone of the formula $$\underset{(CH_2)_n}{\underbrace{CH_2\diagup\overset{CO}{\phantom{X}}\diagdown CH-CH_2-CH_2-R_1}} \qquad I$$

in which $n=2,3$ and $R_1=-CN$, $-COOH$. The ketone (I) is changed to the corresponding hydroperoxide by means of $H_2O_2$, the hydroperoxide is catalytically split by means of a catalyst $Fe^{++}/Cu^{++}$ to give an unsaturated acid of the formula $$HOOC-(CH_2)_3-CH=CH-(CH_2)_2-R_1$$

and this is catalytically hydrogenated to the compound $$HOOC-(CH_2)_n-R_1$$

When $R_1$ is different from Y, $R_1$ is changed to Y through known methods.

10 Claims, No Drawings

PROCESS FOR PRODUCING DIFUNCTIONAL ALIPHATIC ORGANIC COMPOUNDS

This invention relates to a new process for simply and economically producing difunctional aliphatic organic compounds widely used in the chemical industry.

More precisely, this invention relates to the preparation of compounds of formula:

$$X-(CH_2)_n-Y$$

in which n is 6 or 7, X is —COOH or —COOR, Y is —CN, —COOH, —CONH$_2$, —CH$_2$NH$_2$ or —COOR, and R is a linear or branched alkyl of 1 to 6 carbon atoms, using as the starting substance cyanoethyl derivatives of cycloaliphatic ketones such as cyclopentanone and cyclohexanone. Essentially, the new process is represented by the following reaction scheme in which reference is made specifically to the preparation of cyclohexanone derivatives for reasons of clarity, it being apparent that that which is written is equally valid for cyclopentanone:

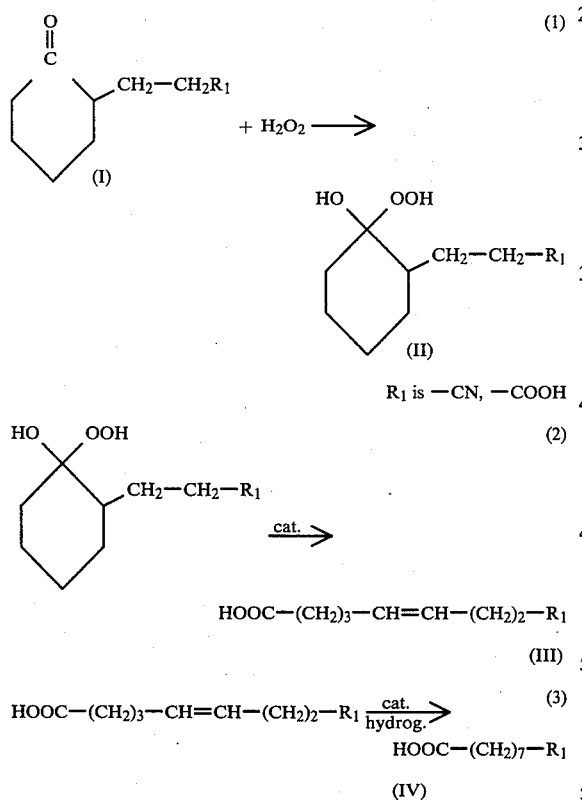

mer and dimer peroxides which can be identified by the following formulas:

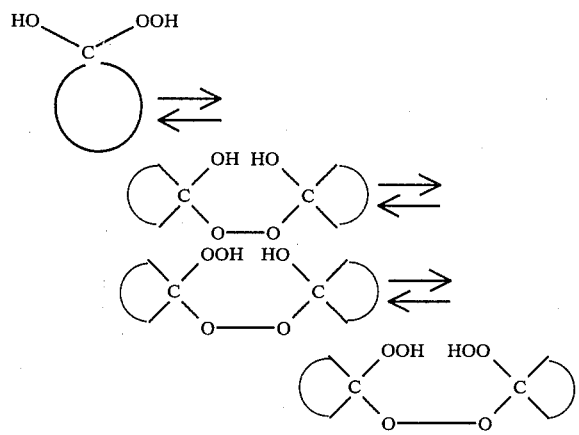

However, this is irrelevant for the purposes of the present process in that all the aforesaid peroxide forms react in a uniform manner in stage (2).

Stage (2) is carried out directly on the reaction mixture from stage (1) without any separation of intermediate products. A catalyst consisting of ferrous salts and cupric salts is added to this mixture, adjusting the addition in order to prevent the temperature of the mixture exceeding 100° C., and preferably such as to maintain it below 50° C. In this respect, the hydroperoxide ring opening reaction is exothermic.

This reaction can be carried out only in an aqueous or aqueous-organic medium.

The organic solvent is chosen for example from the group consisting of methanol, ethanol, dioxane, acetone, acetonitrile, acetic acid and dimethylformamide. The reaction medium used influences the conversion of the ethyl derivative of the cycloaliphatic ketone. In an aqueous-organic medium there is a fairly high conversion, which according to the type and quantity of the chosen organic solvent can reach 90%, whereas in an aqueous medium the conversion is always lower.

The catalyst can be formed from any cupric and ferrous salt. The sulphates are preferably used, but the acetates and nitrates can also be used.

The molar Fe$^{++}$/Cu$^{++}$ ratio lies between 1 and 100, whereas the molar H$_2$O$_2$/Fe$^{++}$ ratio lies between 0.01 and 0.8.

It should be noted that the use of the Fe$^{++}$/Cu$^{++}$ catalyst is absolutely critical if the difunctional compounds (III) are to be obtained from the hydroperoxides (II) in an industrially significant manner. In this respect, if Fe$^{++}$/Fe$^{+++}$ catalysts are used, only traces of useful product are obtained, the ketone mainly becoming converted into mixtures of C$_9$-C$_{18}$ acids of various types.

The reaction proceeds equally using Cu$^{+}$/Cu$^{++}$ catalysts. However, a very low conversion of the cycloaliphatic ketone into the ethyl derivative is obtained, because of which the process is no longer economical. The yield of final product with respect to the converted product is also much lower.

Stage (3), in which the unsaturated difunctional compounds (III) are hydrogenated to the corresponding saturated compounds (IV), is carried out by catalytic hydrogenation in an organic solvent in the presence of Stage (1) is carried out by reacting H$_2$O$_2$ with the ethyl derivative of cyclohexanone in a molar ratio of between 0.5 and 2, and preferably in an equimolecular ratio, in the presence of a small quantity of a mineral acid as catalyst.

The hydrogen peroxide can be used in any concentration. However, a concentration of between 30 and 60% is preferred. The mineral acid used is preferably concentrated H$_2$SO$_4$ in a ratio of 0.1-5% v/v with respect to the volume of the reaction mixture.

The hydroperoxide which forms in stage (1) is in reality not a single compound, but a mixture of mono- Pd, Pt or Ni catalysts, at ambient temperature and ordinary pressure.

Preferred catalysts are Pd, Pt or Raney Ni.

Preferred hydrogenation solvents are the aliphatic alcohols or the aliphatic acids. If it is required to limit the reduction to the double bond, the hydrogenation is stopped when the stoichiometric quantity of hydrogen has been absorbed.

However, if the $R_1$ group is also to be reduced (in particular when $R_1$ is CN), hydrogenation is continued until all the hydrogen stoichiometrically necessary for attaining the required degree of hydrogenation has been absorbed.

When the $R_1$ radical in the final hydrogenated product (IV) is a —CN group which it is required to hydrolyse to —CONH$_2$ or —COOH, the product is subjected to normal hydrolysis with an aqueous alkaline hydrate by heating under reflux. Alternatively, the hydrolysis can be carried out before the hydrogenation stage (3) under the same conditions.

The final yield of product of formula (I) with respect to the ethyl derivative of the converted initial cycloaliphatic ketone is always around 90%.

The starting substance in the process according to the present invention, cyclohexanonepropionitrile, is prepared by known methods from cyclohexanone and acrylonitrile, these both being compounds widely available commercially at low cost:

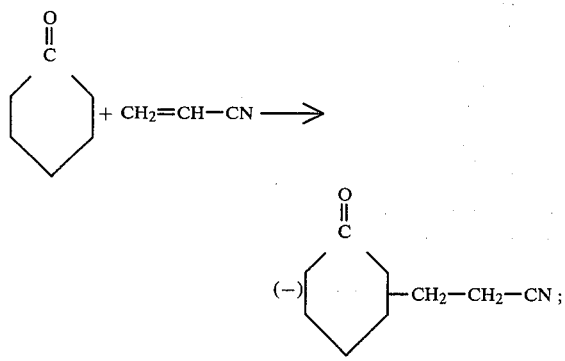

It is preferably prepared from cyclohexanone and acrylonitrile in a molar ratio of 1:0.5 in the presence of an amine and a carboxylic acid as catalysts, together with a small quantity of hydroquinone which during heating to 130°–150° C. prevents polymerisation of the acrylonitrile (Nishimura et al Hokkaido Daigaten Koga-Kubu-Ken-Kyn Hokoku 109 (1970) C.A. 74,124944 (1971)).

As initially stated, the cyclohexanonepronepionitrile can be hydrolyzed to the corresponding acid before being reacted with the hydrogen peroxide in stage (1) of the process according to the invention. In this case, the final product of the process is a dicarboxylic acid containing 8 or 9 carbon atoms which can if required be esterified by reaction with an alcohol in the presence of a condensing agent.

Alternatively, stage (1) can be carried out in the presence of an alcohol to directly give the final compound in which Y is COOR. However, by operating in this manner, only one of the terminal carboxyls is esterified, and if total esterification is required, the hemiester must be separated, and the other carboxyl must be esterified with an alcohol in an anhydrous environment in the presence of a condensing agent.

It has been found that during stage (2) of the process according to the present invention in which the hydroperoxide ring is opened, in addition to the compounds (II) small quantities are formed of compounds of the formula:

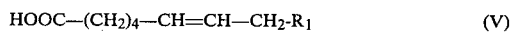

and of compounds of the formula

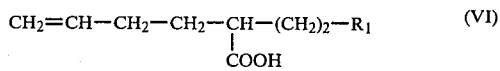

in which $R_1$ is as heretofore defined.

However, the formation of compound (V) is completely irrelevant for the purposes of the described process, in that during the subsequent catalytic reduction stage (3), this compound behaves exactly as the compound (III), and therefore leads to the same final product (IV).

The by-product (VI), which is always formed in a very small quantity and in any case never exceeding 20% of the total product, is easily eliminated at the end of stage (2) by fractional distillation or crystallisation.

As stated initially, the great importance of the process according to the present invention is that starting from widely available low-cost raw materials such as cyclohexanone, acrylonitrile and hydrogen peroxide, it is possible to obtain products of great interest in the synthetic fiber, thermoplastics and plasticiser fields, such as azelaic acid and 9-aminononanoic acid, which are products which cannot be prepared economically by any other known process. Some non-limiting examples in which all the operating details are given are described hereinafter in order to make the process according to the present invention more easily reproducible.

EXAMPLE 1

2.2 g of 59% H$_2$O$_2$ in the presence of 0.2 ml of 75% sulphuric acid are added to 5.7 g of cyclohexanonepropionitrile. This is left stirring for 10 minutes, and after this time a 10% aqueous solution of H$_2$SO$_4$ containing 3 g of CuSO$_4$.5H$_2$O are slowly added.

Under continued stirring, 11 g of FeSO$_4$.7H$_2$O are gradually added over a period of 15 minutes. The temperature rises spontaneously from 18° to 32° C., and the mixture is kept under further stirring for 15 minutes. The aqueous solution is extracted with CH$_2$Cl$_2$, and the organic phase is treated with an aqueous solution of NaOH. The solvent is evaporated from the CH$_2$Cl$_2$ solution to give 3.5 g of cyclohexanonepropionitrile, which can be recycled, whereas 2.2 g of acid product are recovered from the aqueous solution after acidifying.

The acid product thus prepared is dissolved in 20 ml of methanol, and 0.1 g of Pd on carbon are added. Hydrogen is introduced at ambient temperature until 0.026 g have been absorbed. The methanol is evaporated to dryness, and the separated product is dissolved in 15 g of 10% aqueous NaOH. The mixture is left under reflux for 2 hours, and is then cooled and acidified with 10% sulphuric acid. 2.4 g of azelaic acid are obtained on crystallising the product from water.

Conversion of the cyclohexanonepropionitrile 39%. Yield of azelaic acid with respect to the converted product 87%.

The same example was repeated in an identical manner, but using 11 g of $FeSO_4.7H_2O$ and 5 g of $Fe_2(SO_4)_3$ as catalyst. Only traces of azelaic acid were obtained, which were difficult to separate from a mixture of saturated and unsaturated acids containing 9 and 18 carbon atoms.

EXAMPLE 2

The test of example 1 was repeated, with the exception of the final part. The acid product (2.2 g) which was separated after extraction with $CH_2Cl_2$ was dissolved in acetic acid, 0.1 g of $PtO_2$ was added and the mixture subjected to selective hydrogenation at ambient temperature and ordinary pressure until the stoichiometric quantity of hydrogen for the azelaic acid had been absorbed. Yield with respect to the converted product 85%.

EXAMPLE 3

The test of example 1 was repeated, with the exception that the 2.2 g of acid product obtained from the extraction with $CH_2Cl_2$ were dissolved in methanol, 0.1 g of $PtO_2$ and 2 g of gaseous $NH_3$ were added, and the mixture then hydrogenated at ambient temperature and ordinary pressure until hydrogen absorption ceased. 1.8 g of 9-aminononanoic acid were obtained, equal to a yield of 82% with respect to the converted product.

EXAMPLE 4

2.2 g of 30% $H_2O_2$ in the presence of 0.2 ml of 75% $H_2SO_4$ are added to 5.7 g of cyclohexanonepropionitrile.

The reaction is allowed to proceed for 10 minutes under stirring, and the mixture is then poured into 10 ml of acetonitrile containing 3 g of cupric acetate.

11 g of $FeSO_4.7H_2O$ are added to this solution over a period of 15 minutes. The temperature rises spontaneously to 38° C., and stirring is continued for a further 30 minutes. After this period the solution is cooled and extracted with 50 ml of ethyl acetate. The solvent is evaporated, and 3 g of cyclohexanonepropionitrile and 2.7 g of an unsaturated acid product are obtained by fractional distillation.

The conversion of the cyclohexanonepropionitrile is thus 47%. The distilled acid product is dissolved in 10% NaOH and heated under reflux for 2 hours. The solution is acidified, and the precipitated acid product is dissolved in ethyl alcohol. 0.1 g of Pd on carbon is added, and the mixture then subjected to hydrogenation at ordinary pressure and temperature until hydrogen absorption ceases. 3.2 g of azelaic acid are obtained, equal to a yield of 86% with respect to the converted product.

EXAMPLE 5

5 g of cyclohexanonepropionitrile are mixed at ambient temperature with 1.7 ml of 59% hydrogen peroxide.

The solution is added to 25 ml of methanol containing 2 ml of concentrated sulphuric acid, and the mixture is poured under stirring into a solution of 2 g of cupric acid monohydrate and 5 g of $FeSO_4.7H_2O$ in 25 ml of water. The addition is made over 5 minutes, and the temperature rises spontaneously from 18° to 45° C. After 30 minutes the mixture is cooled, and extracted with 50 ml of chloroform.

The chloroform extract is treated with 10% NaOH, and 36 g of unsaturated acid product are recovered from the aqueous alkaline solution by acidification. This product is hydrolysed by prolonged heating under reflux with 10% NaOH. The acid is precipitated by acidification with 10% $H_2SO_4$, and is dissolved in methanol, and 3 g of ammonia and 0.1 g of $PtO_2$ are added. Hydrogenation is carried out at ordinary temperature and pressure until there is no further absorption of hydrogen. 4 g of azelaic acid are obtained. 1.3 g of cyclohexanonepropionitrile are recovered by eliminating the solvent from the chloroform solution previously set aside, to give a calculated yield with respect to the converted product of 88%.

The test was repeated in an identical manner, but using 2 g of cupric acetate and 4 g of cuprous acetate as catalyst. A cyclohexanonepropionitrile conversion of 20% was obtained, and an azelaic acid yield of 70% with respect to the converted product.

EXAMPLE 6

5 g of cyclohexanonepropionitrile are hydrolysed to cyclohexanonepropionic acid by heating under reflux with 20 ml of a 1:1 solution of acetic acid/concentrated hydrochloric acid for 3 hours. The mixture is extracted with $CH_2Cl_2$, and the separated acid is mixed with 1.7 g of 59% $H_2O_2$. The solution is added to 25 ml of methanol containing 2 ml of concentrated $H_2SO_4$, and the process is carried out as described under example 5.

A cyclohexanonepropionic acid conversion of 65% is obtained, with an azelaic acid yield of 88% with respect to the converted product.

EXAMPLE 7

5 g of cyclohexanonepropionitrile mixed with 1.7 ml of 59% $H_2O_2$ are poured into 100 ml of methanol containing 20 ml of concentrated $H_2SO_4$. The procedure described in example 5 is then followed exactly, and the unsaturated ester is hydrogenated in accordance with example 2. The methyl ester of the azelaic heminitrile is obtained with a cyclohexanonepropionitrile conversion of 52%, and a yield of 85% with respect to the nitrile-converted product.

EXAMPLE 8

4.1 g of the methyl ester obtained in example 7 are heated under reflux in 30 ml of methanol and 3 ml of concentrated sulphuric acid for 5 hours. The mixture is diluted with 100 ml of water, and 4.2 g of the methyl ester of azelaic acid are extracted with $CH_2Cl_2$.

What we claim is:

1. A process for producing difunctional aliphatic organic compounds of formula $X—(CH_2)_n—Y$ in which n is 6 or 7, X is —COOH, or —COOR, Y is —CN, —COOH, —CONH$_2$, —CH$_2$NH$_2$ or —COOR, where R is a linear or branched alkyl containing 1 to 6 carbon atoms, wherein a compound of formula

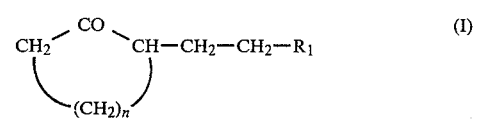

(I)

in which n is 2 or 3 and $R_1$ is —CN or —COOH, is reacted with $H_2O_2$; the obtained hydroperoxide of formula

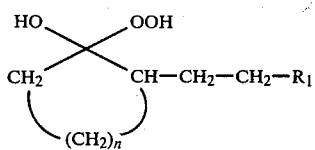 (II)

in which n and $R_1$ are as heretofore defined, is catalytically split in an aqueous or aqueous-organic medium by means of a catalyst of $Fe^{++}/Cu^{++}$ type to give a compound of formula $$HOOC-(CH_2)_3-CH=CH-(CH_2)_2-R_1 \quad (III)$$

in which $R_1$ is as heretofore defined, and the unsaturated acid thus produced is catalytically hydrogenated at ambient temperature and ordinary pressure to the compound $$HOOC-(CH_2)_n-R_1 \quad (IV)$$

in which n and $R_1$ are as heretofore defined, the radical $R_1$ being converted into the radicals Y, if the radicals Y are different from $R_1$.

2. A process as claimed in claim 1, wherein compound (I) is reacted with $H_2O_2$ in a molar ratio of between 0.5 and 2, in the presence of a small quantity of a mineral acid as a catalyst.

3. A process as claimed in claim 1, wherein the hydroperoxide (II) is split by gradually adding a ferrous salt at a temperature of between 10° and 100° C., with a $H_2O_2/Fe^{++}$ ratio of between 0.01 and 0.8, and a $Fe^{++}/Cu^{++}$ ratio of between 1 and 100.

4. A process as claimed in claim 3, wherein the ferrous salt is chosen from the group consisting of sulphate, nitrate and acetate.

5. A process as claimed in claim 3, wherein the cupric salt is chosen from the group consisting of sulphate, nitrate and acetate.

6. A process as claimed in claim 1, wherein the unsaturated acid (III) is catalytically hydrogenated in the presence of a catalyst chosen from the group consisting of Pt, Pd and Ni.

7. A process as claimed in claim 1, wherein the acid (IV) in which R is —CN is hydrolyzed to the corresponding compound in which Y is —$CONH_2$ or —COOH by heating under reflux with an aqueous alkaline hydrate.

8. A process as claimed in claim 1, wherein the acid (IV) in which $R_1$ is —CN, is reduced to the corresponding compound in which Y is —$CH_2 NH_2$ is catalytic hydrogenation in the presence of a Pt, Pd or Ni catalyst at ambient temperature and ordinary pressure.

9. A process as claimed in claim 1, which is carried out in the presence of an aliphatic alcohol of formula R—OH so as to directly obtain compounds in which Y is —COOR.

10. A process as claimed in claim 1, wherein the product (IV) in which X is —COOH is esterified under known conditions with an alcohol of formula R—OH to give the corresponding compound in which X is —COOR.

* * * * *